United States Patent
Yao et al.

(10) Patent No.: US 9,284,585 B2
(45) Date of Patent: Mar. 15, 2016

(54) METHOD FOR INCREASING YIELD OF TOTAL FLAVONOIDS IN GANODERMA LUCIDUM MYCELIUM

(71) Applicants: SHANDONG QIHE BIO-TECHNOLOGY CO., LTD, Zibo (CN); INSTITUTE OF AGRICULTURAL RESOURCES AND ENVIRONMENT, SHANDONG ACADEMY OF AGRICULTURAL SCIENCES, Jinan (CN)

(72) Inventors: Qiang Yao, Jinan (CN); Zhiyuan Gong, Jinan (CN); Jianchang Su, Zibo (CN); Zhaohui Liu, Jinan (CN); Jilei Wang, Zibo (CN); Xingcheng Du, Zibo (CN); Xiao Liu, Jinan (CN); Xiaoyan Zhu, Zibo (CN); Qingxin Zhou, Jinan (CN); Shan Zhu, Jinan (CN); Yanwen Yang, Jinan (CN)

(73) Assignees: SHANDONG QIHE BIO-TECHNOLOGY CO., LTD, Jinan (CN); INSTITUTE OF AGRICULTURAL RESOURCES AND ENVIRONMENT, SHANDONG ACADEMY OF AGRICULTURAL SCIENCES, Jinan (CN)

( * ) Notice: Subject to any disclaimer, the term of this patent is extended or adjusted under 35 U.S.C. 154(b) by 109 days.

(21) Appl. No.: 14/373,381

(22) PCT Filed: Apr. 7, 2013

(86) PCT No.: PCT/CN2013/000394
§ 371 (c)(1),
(2) Date: Jul. 21, 2014

(87) PCT Pub. No.: WO2013/155868
PCT Pub. Date: Oct. 24, 2013

(65) Prior Publication Data
US 2015/0010964 A1 Jan. 8, 2015

(30) Foreign Application Priority Data
Apr. 16, 2012 (CN) .......................... 2012 1 0110969

(51) Int. Cl.
C12P 17/06 (2006.01)
C12N 1/14 (2006.01)
C12N 1/38 (2006.01)

(52) U.S. Cl.
CPC . *C12P 17/06* (2013.01); *C12N 1/14* (2013.01); *C12N 1/38* (2013.01)

(58) Field of Classification Search
None
See application file for complete search history.

(56) References Cited

PUBLICATIONS

Lakshmi et al. Antimutagenic activity of methanolic extract of Ganoderma lucidum and its effect on hepatic damage caused by benzo[a]pyrene. Journal of Ethnopharmacology 2006, vol. 107, pp. 297-303.*
Sheena et al. Antibacterial Activity of Three Macrofungi, Ganoderma lucidum, Navesporus floccosa and Phellinus rimosus Occurring in South India, Pharmaceutical Biology 2003, vol. 41, No. 8, pp. 564-567.*

* cited by examiner

*Primary Examiner* — Louise W Humphrey
*Assistant Examiner* — Christopher Keller
(74) *Attorney, Agent, or Firm* — CBM Patent Consulting, LLC

(57) ABSTRACT

A method for increasing the yield of total flavonoids in *Ganoderma lucidum* mycelium by an expansin comprises: (1) inoculating *Ganoderma lucidum* into the PD liquid fermentation medium, activating the culturing of the strains and obtaining a seed solution; (2) inoculating the seed solution into a liquid fermentation medium, culturing and adding the expansin solution, then further culturing, isolating and obtaining *Ganoderma lucidum* mycelium; (3) extracting flavonoids from the *Ganoderma lucidum* mycelium and obtaining total flavonoids. A plant expansin is used for the liquid fermentation production of flavonoids ingredients of *Ganoderma lucidum*, and the fermentation process and extraction method are optimized to increase greatly the yield of total flavonoids in *Ganoderma lucidum*.

7 Claims, 1 Drawing Sheet

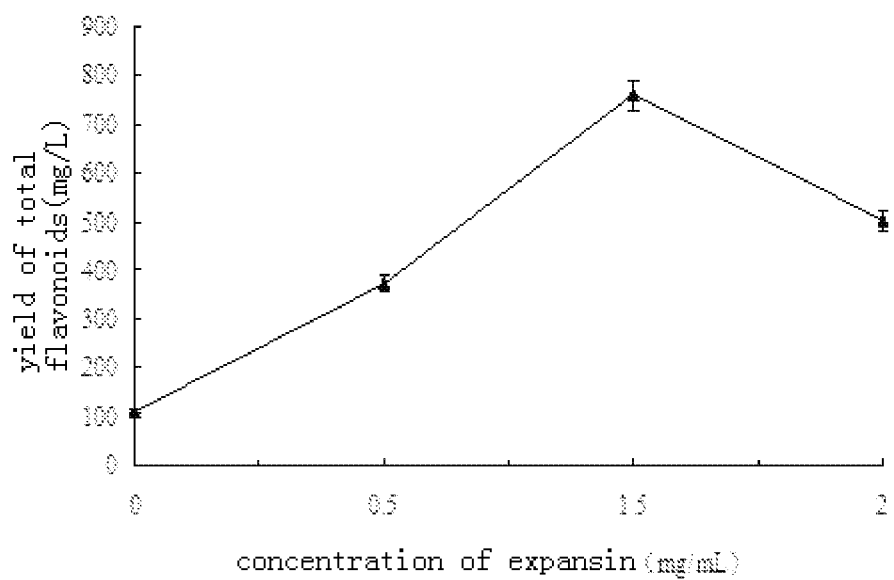

METHOD FOR INCREASING YIELD OF TOTAL FLAVONOIDS IN *GANODERMA LUCIDUM* MYCELIUM

This application is the U.S. national phase of International Application No. PCT/CN2013/000394 Filed on 7 Apr. 2013 which designated the U.S. and claims priority to Chinese Application Nos. 201210110969.5 filed on 16 Apr. 2012, the entire contents of each of which are hereby incorporated by reference.

TECHNICAL FIELD

The present invention relates to a method for increasing the yield of total flavonoids in *Ganoderma lucidum* mycelium by an expansin, which belongs to biotechnology fermentation engineering field.

BACKGROUND

*Ganoderma lucidum*, the general name for *Ganoderma lucidum* karst and *Ganoderma japonicrn* L. loyd, belongs to Polyporaceae family, *Ganodelma* genus. With the effect of strengthening healthy, it is considered as a treasure in Shen Nong's Herbal. As a Chinese traditional precious medicinal herb used for thousands of years, *Ganoderma lucidum* has a very high medical value. After decades of modern pharmacology studies by research institutions, it is confirmed that *Ganoderma lucidum* has remarkable therapeutic effects in enhancing human immunity, regulating blood glucose, controlling blood pressure, assisting tumor radiotherapy and chemotherapy, protecting liver, promoting sleep and so on. Medical certificates that *Ganoderma lucidum*, *Ganoderma sinense* and *Coriolus versicolor* have the highest medicinal value. Recent years, chemical elements and clinical studies on *Ganoderma* fungi are more and more. The effects of flavonoids thereof are in many ways. Flavonoids are strong antioxidants which can effectively clear up the oxygen free radical in organism. The ability of flavonoids to prevent oxidation is ten times more than the vitamin E, which can prevent cell degradation and aging, and cancer occurring. Natural flavonoids compounds mostly exist in the form of glycosides, different flavonoid glycosides can be formed as the kinds, numbers, connecting locations and connecting modes of sugars are different. In twentieth Century late eighties, flavonoids were noticed as a health product for the first time by the international medical community. Experiments demonstrated that flavonoids of *Ganoderma lucidum* can improve blood circulation, lower cholesterol, improve the symptoms of cardiovascular disease, lower blood sugar by 26% and tri-Glycerides by 39%, stable collagen, and play good roles in retinopathy and blood capillary fragility caused by diabetic.

At present, more than 10 kinds of flavonoids compounds have been isolated from *Ganoderma lucidum*, including flavones, flavonols, flavanones and so on. However, the production of flavonoids in *Ganoderma lucidum* becomes the limiting factor for inhibiting its application. In natural word, the wild *Ganoderma lucidum* is very rare and cannot meet people's needs. It is an effect method to produce active pharmaceutical ingredients of *Ganoderma lucidum* by fluid fermentation, because this method has the advantages of short production cycle, less labor and small impact by the external environment. Studies at home and abroad are mainly about the culturing of *Ganoderma lucidum* mycelium to produce active pharmaceutical ingredients, and the industrial applications are mainly concentrate on the technical aspects such as fermentation condition, product extract and separation, etc., and the total fermentation level is low.

Chinese patent CN1264743A (application No. 00111953.2) discloses a liquid fermentation method for preparing ganoderic polysaccharide and ganoderic acid. In the method, the bacterial strain *Ganoderma lucidum* (Leyss exFr.) Karst. is used as its microbe, and the aerobic liquid fermenting process, the aerobic liquid fermentation-static liquid culture method, or static liquid culture process is used for production ganoderic exopolysaccharide, ganoderic intracellular polysaccharide and ganoderic acid. Its advantages are high gandoric acid content up to 2.8 mg/100 mg, high total polysaccharide content up to 2.34 g/L. The method needs static culturing to induce synthesizing production. The fermentation period is long, and the total fermentation time including liquid aerobic fermentation and static culturing is more than 20 days. The overall producing efficiency is low, which could not meet the need of modern industrial fermentation and production. There is no report about the high yielding liquid fermentation and extraction technologies of *Ganoderma lucidum* flavonoids component, which even more limits its development of industrial application.

Expansin is a new type of protein species found in plant cell walls in the recent years. Expansin is first obtained by separating and purifying the elongation field of cucumber hypocotyl. It has been proved that expansin is also existing in the cell wall of oat coleoptile, Trichosanthes kirilowii root tip, tomato, strawberry, arabidopsis, paddy, cotton fibrin, corn, soybean, etc, and is considered existing in various dicotyledonous and monocotyledonous plant cell walls. It is considered that expansin is related to promoting the cell physiological growth, affecting the physiological growth processes such as vegetative growth, morphogenesis, pollination and fertilization, and fruit softening, etc. Experiments about cell wall recombination have shown that expansin has the function of recovering the thermal inactivated cell wall in vitro to extend, which is different with other enzyme proteins for cell wall found formerly. It is supposed that expansin can regulate physiological activities such as acid-dependent cell wall extension and stress relaxation by breaking the hydrogen bonds between the cell wall polymers, and may be an important regulatory factor for physiological regulation and cell wall extension process in the period of plant growth. However, there is yet no unambiguous study conclusion of the function mechanism of expansin at home and abroad. Currently there is no report at home and abroad about that the expansin is applied in liquid fermentation of *Ganoderma lucidum* for increasing the yield of flavonoids ingredients.

SUMMARY OF THE INVENTION

In view of the defects of the prior art, the present invention aim to provide a method for increasing the yield of the yield of total flavonoids in *Ganoderma lucidum* mycelium by an expansin.

The technical scheme of the present invention is as follows.

A method for increasing the yield of total flavonoids in *Ganoderma lucidum* mycelium, comprises the following steps of:

(1) inoculating *Ganoderma lucidum* strains into the PD liquid fermentation medium and performing activation culture to obtain a seed liquid;

(2) inoculating the seed liquid obtained in step (1) into a liquid fermentation medium to a volume ratio of 5~10% to perform liquid fermentation culture at 25~30° C. for 3~5 days, then adding an expansin solution to a concentration of 0.3~2.0 mg/mL to perform further culture for 5~7 days, and separating to obtain *Ganoderma lucidum* mycelium;

(3) extracting flavonoids ingredients from the *Ganoderma lucidum* mycelium obtained in the step (2) so as to obtain total flavonoids.

Preferably, according to the invention, each liter of the PD liquid fermentation medium in the step (1) comprises the following components:

peeled potato 200 g, glucose 20 g, diluted to 1000 mL by distilled water.

According to the invention, the preferred activation culture in the step (1) is processed in the darkroom with a shaking speed of 100~180 r/min at 25~30° C. for 3~5 days.

Preferably, according to the invention, the liquid fermentation medium in the step (2) has a pH of 6.0 and each liter of the medium comprises the following components:

lactose 20 g, sucrose 20 g, soybean powder 25 g, peptone 2 g, yeast extract 1 g, $MgSO_4 \cdot 7H_2O$ 0.5 g, $KH_2PO_4$ 0.5 g, diluted to 1000 mL by water.

Preferably, according to the invention, the expansin concentration in the step (2) is 0.5~2.0 mg/mL; further preferably, 0.75~1.75 mg/mL; most preferably, the expansin concentration in the step (2) is 1.5 mg/mL.

The preparation of the expansin solution in the step (2) may refer to the prior technique, such as the method described in "Two endogenous proteins that induce cell wall extension in plants. McQueen-Mason et al. Plant Cell, 1992, 4: 1425~1433. McQueen-Mason S J, Durachko D M, Cosgrove D J". The expansin solution in step (2) may also be prepared by the method which comprises the following steps:

sterilizing a broad bean or cucumber seed for 4~6 minutes with 0.05~0.15 wt. % mercury chloride ($HgCl_2$), washing with running water for 5~7 hours, culturing in the darkroom for 4~6 days at 15~28° C., taking 3~4 cm of seedling hypocotyl apices, precooling for 0.5 hours at −20° C., adding a homogenate buffer solution that is pre-cooled to 4° C., filtering with a nylon net having an aperture of 70 µm after homogenate, washing the filter residue with a homogenate buffer solution, adding the filter residue in the homogenate buffer solution, settling for 1~3 hours to obtain a settled solution, adding an extracting solution in the settled solution, extracting for 44~50 hours at 4° C., slowly adding 0.3~0.5 g/mL ammonium sulfate (($NH_4)_2SO_4$) in the filtrate while stirring to prevent a partial supersaturation of the ($NH_4)_2SO_4$, settling for 45~50 hours, centrifuging for 5~10 minutes at 4° C., dissolving the sediment with an acid buffer solution, dialyzing in a dialysis bag with a molecular weight of 3000 Da at 4° C., centrifuging the dialyzate at 20000 g for 10 minutes, and taking the supernatant so as to obtain the expansin solution.

In the above preparation method of the expansin solution, the homogenate buffer solution has a pH of 7.0, and comprises 25 mmol/L HEPES (4-(2-hydroxyethyl)-1-piperazineethanesulfonic acid), 1.5 mmol/L $Na_2S_2O_5$, 2 mmol/L EDTA and 0.1 wt. % Triton X-100. The extracting solution has a pH of 6.0, and comprises 15 mmol/L 4-(2-hydroxyethyl)-1-piperazineethanesulfonic acid, 1.0 mmol/L EDTA, 1.5 mmol/L $Na_2S_2O_5$ and 0.5 mmol/L NaCl. The acid buffer solution is prepared by dissolving 2.05 g of sodium acetate in water, adjusting pH to 4.0 with glacial acetic acid, and adding water to 1 L.

Preferably, according to the invention, the separation in the step (2) is carried out by centrifuging with a rotate speed of 15000 r/min at 4° C. for 10 minutes.

Preferably, according to the invention, the method of extracting flavonoids ingredients from the *Ganoderma lucidum* mycelium in the step (3) may refer to the method described in "Xiaojun Fan, et al. Research of the technique of extracting total flavonoids from Leaves of Taxodium distichum with ultrasonic. Gansu Agriculture Science and Technique. 2008, (11): 13~14". It also may be performed as the method which comprises the following steps of:

drying *Ganoderma lucidum* mycelium obtained in the step (2) at 65 and grinding to power, adding ethanol solution of 70~80% volume concentration and extracting by ultrasonic at 40 kHz and 200 W, 60~70 for 3~5 hours, then filtrating and separating the filtrate, taking the deposit and repeating 2~3 times of the extract step with ultrasonic and the filtration step mentioned as above, incorporating the filtrate so as to obtain flavonoids ingredients.

Compared with the prior art, the present invention has the following advantages:

1. A plant expansin is applied in the liquid fermentation production of flavonoids ingredients of *Ganoderma lucidum* in the present invention, and the fermentation process and extraction method are optimized to increase greatly the yield of total flavonoids in *Ganoderma lucidum* and to achieve a yield per liter of fermentation broth of 760.1 mg. The total flavonoids extraction can be used directly for immunity regulation, anti-tumor, hypoglycemic drug preparation, and the technical process of the invention and the method is also suitable for large-scale production of fermentation tank. In general, the method has good industrial application prospect.

2. The invention adopts the method of the liquid fermentation of *Ganoderma lucidum* mycelium, which has the advantages of simple extracting method, good repeatability, high-yield, no need the steps such as static culturing to induce synthesizing product, short-cycle, high production efficiency, using natural product as raw material, environmental protection without toxic, and low cost. The whole fermentation process is controllable, not limited by the external environmental conditions, and very suitable for industrial production and application. *Ganoderma lucidum* fermentation strain of the invention can also be applied to other ordinary Cordyceps militaris cultivated varieties.

3. The expansin mentioned in the invention can be extracted from most dicotyledonous and monocotyledonous plants, and fungi, etc, which is widely available and low cost. The preferred method of the invention is relatively simple, so it can be applied for scale extraction production and also has a good effect on promoting the active substance production of *Ganoderma lucidum* such as flavonoids ingredients.

FIGURE DESCRIPTION

FIG. 1 is the curve of the different concentrations of expansin solution effect on the output of the total flavonoids of *Ganoderma lucidum* mycelium.

EMBODIMENT

The following is the detail description of the present invention with reference to examples, but the scope of the present invention is not limited thereto.

Raw Materials and Medium

*Ganoderma lucidum* fermentation strains described in the examples is selected from Taishan *Ganoderma lucidum* (*Ganoderma lucidum*) with Culture Collection Number of CGMCC No. 5.644 and Xinzhou *Ganoderma lucidum* (*Ga-* noderma lucidum) with Culture Collection Number of CGMCC No. 5.534, which are purchased from China General Microbiological Culture Collection Center.

Rutin standard material described in the examples is purchased from Jinan Shengwei Biotechnology Co., Ltd. Other reagents are all conventional commercial products.

The expansin solution of examples can be prepared by the method which comprises the following steps of:

sterilizing the soybean (Glycine max L. Merr. CV. M40; purchased from Jinan Weili Seed Industry Co., Ltd) or cucumber seed (Cucumis sativus L. CV Jinnian No 6; purchased from Jinan Weili Seed Industry Co., Ltd.) with 0.1 wt % $HgCl_2$ for 5 minutes, washing with running water for 6 h, planting in wet vermiculite, dark culturing for 4 days at 27° C., taking 3~4 cm of seedling hypocotyl apices, e.g. growing area that about 100 g, setting at −20° C. for 0.5 hour to pre-cool, adding homogenate buffer solution that pre-cooled to 4° C., filtering with a nylon net having an aperture of 70 μm after high speed dividing, washing the filter residue with homogenate buffer solution, adding the filter residue in the homogenate buffer solution, settling for 2 hours to obtain a settled solution, adding an extracting solution in the settled solution, extracting for 48 hours at 4° C., slowly adding 0.4 g/mL ammonium sulfate (($NH_4)_2SO_4$) in the filtrate while stifling to prevent a partial supersaturation of the $(NH_4)_2SO_4$, settling for 28 hours, centrifuging at 25000 g at 4° C. for 10 minutes, dissolving the sediment with an acid buffer solution, dialyzing in a polyvinylidene fluoride (PVDF) dialysis bag (purchased from Beijing Lubrizol Wright Science and Technology Co., Ltd.) with a molecular weight of 3000 Da at 4° C., centrifuging at 20000 g the dialyzate for 10 minutes, taking the supernatant so as to obtain the expansin solution and reserving at 4° C. Other steps that are not described can consult the descriptions in "Two endogenous proteins that induce cell wall extension in plants. McQueen-Mason et al. Plant Cell, 1992, 4: 1425~1433. McQueen-Mason S J, Durachko D M, Cosgrove D J".

The homogenate buffer solution mentioned as above has a pH of 7.0, and comprises 25 mmol/L HEPES (4-(2-hydroxyethyl)-1-piperazineethanesulfonic acid), 1.5 mmol/L $Na_2S_2O_5$, 2 mmol/L EDTA and 0.1 wt. % Triton X-100.

The extracting solution has a pH of 6.0, and comprises 15 mmol/L 4-(2-hydroxyethyl)-1-piperazineethanesulfonic acid, 1.0 mmol/L EDTA, 1.5 mmol/L $Na_2S_2O_5$ and 0.5 mmol/L NaCl.

The acid buffer solution is prepared by dissolving 2.05 g of sodium acetate in water, adjusting pH to 4.0 with glacial acetic acid, and adding water to 1 L.

The concentration determination of the expansin solution can employ Coomassie brilliant blue method, which may specifically refer to the operations of Coomassie blue method described in "Quintessence of Protein Science Laboratory Manual" (ISBN: 703018086, publication date: 1900-1-1), by using bovine serum albumin as the standard curve. The expansin concentration of the expansin solution detected by the above method and the result is 0.31 g/mL.

Each liter of the PD liquid fermentation medium described in examples comprises the following components: peeled potato 200 g, glucose 20 g, diluted to 1000 ml with distilled water.

The liquid fermentation medium described in Examples has a pH of 6.0 and each liter of the medium comprises the following components: lactose 20 g, sucrose 20 g, soybean powder 25 g, peptone 2 g, yeast extract 1 g, $MgSO_4 \cdot 7H_2O$ 5 g, $KH_2PO_4$ 0.5 g, diluted to 1000 mL by water.

Example 1

A method for increasing the yield of total flavonoids in *Ganoderma lucidum* mycelium, comprises the following steps of:

(1) inoculating Taishan *Ganoderma lucidum* (*Ganoderma lucidum*) strains which has a strain number of CGMCC No. 5.644 into the PD liquid fermentation medium to perform activation culture in the darkroom with a shaking speed of 150 r/min at 28° C. for 3 days so as to obtain a seed liquid;

(2) inoculating the seed liquid obtained in step (1) into a liquid fermentation medium to a volume ratio of 10% to perform liquid fermentation culture at 30° C. for 3 days, then adding an expansin solution to a concentration of 0.5 mg/mL to perform further culture for 7 days, centrifuging at 15000 r/min for 10 minutes, separating to obtain the *Ganoderma lucidum* mycelium;

(3) drying *Ganoderma lucidum* mycelium from 1 L fermentation broth in the step (2) at 65° C. to obtain 1314.7 mg, grinding to power, adding 100 mg mycelium powder of *Ganoderma lucidum* into 2 mL ethanol solution of 70% volume concentration and extracting with 40 kHz and 200 W ultrasonic power at 65° C. for 3 hours, then filtrating and separating the filtrate, sealing the filtrate and reserving it at 4° C., taking the deposit and repeating 3 times of the ultrasonic extraction and filtration steps mentioned as above, incorporating the filtrate so as to obtain total flavonoids.

Preparation of Total Flavonoids Samples

The total flavonoids samples is prepared by adding the flavonoids ingredients from 1 L fermentation broth into ethanol solution of 70% volume concentration and diluting to 50 mL.

Determination of Total Flavonoids

Conventional colorimetry method in the art may be used, which can be referred to "Biochemistry experiment method and technology. ISBN: 978-7-03-010685-8, 2009-07".

(1) Establishment of Standard Curve

The standard curve can be built by the method which comprises the following steps of: weighing up 0.5 g of the rutin standard, placing into 25 ml volumetric flask, dissolving it into 30% v/v ethanol solution, diluting to the gradation, accurately sucking up 10 mL into 100 ml volumetric flask, diluting to the gradation by distilled water, shaking up to uniform, and obtaining 2.0 mg/ml rutin standard solution. Accurately sucking up 0 mL, 1 mL, 2 mL, 3 mL, 4 mL, 5 mL, 6 mL, 7 mL standard solution into 25 mL tubes respectively, and adding 30% v/v ethanol solution to 6 mL, then adding 1.0 mL 5% sodium nitrite solution separately, shaking to uniform, placing for 5 minutes, again adding 1 ml 10 wt % aluminium nitrate solution separately, shaking to uniform, placing for 5 minutes, furthermore, adding 10 ml 1 wt % sodium hydroxide separately, then diluting to the gradation by 30% v/v ethanol solution respectively. Taking the standard solution of 0 ml tube as control, and measuring the absorbance at 510 nm wavelength. Setting the absorbance as X-coordinate and the total content of flavonoids as Y-coordinate so as to obtain the standard curve.

(2) Determination of the Yield of Total Flavonoids

The yield of total flavonoids is determined by the method which comprises the following steps of: taking 0.5 mL total flavonoids sample to be measured into 25 ml tubes, diluting it to 6 mL with 30% v/v ethanol solution, adding 1.0 mL 5% sodium nitrite solution, shaking to uniform, placing for 5 minutes, again adding 1 ml 10 wt % aluminium nitrate solution, shaking to uniform, placing for 5 minutes, furthermore, adding 10 ml 1 wt % sodium hydroxide, then diluting to the gradation by 30% v/v ethanol solution. Taking the sample which only add 6 ml 30% v/v ethanol solution to the gradation as control, and measuring the absorbance at 510 nm wavelength. According to the standard curve, the content of total flavonoids of the measured sample is calculated to be 3.726 mg, i.e. the yield of total flavonoids per liter flavonoids fermentation solution is: 3.726 mg×100=372.6 mg. The result is shown in FIG. 1.

Example 2

It is the same as the method described in Example 1, except that in the step (2) the liquid fermentation culture is performed at 30° C. for 4 days, then adding an expansin solution to a concentration of 1.5 mg/mL to perform further culture for 6 days.

After calculated with the standard curve, the total flavonoids in the sample is 7.601 mg, i.e. the content of total flavonoids per liter fermentation broth is: 7.601×100=760.1 mg (calculating value×100=the content of total flavonoids per liter fermentation broth). The result is shown in FIG. 1.

Example 3

It is the same as the method described in Example 1, except that in the step (2) the liquid fermentation culture is performed at 30° C. for 5 days, then adding an expansin solution to a concentration of 2.0 mg/mL to perform further culture for 5 days.

After calculated with the standard curve, the total flavonoids in the sample is 5.017 mg, i.e. the content of total flavonoids per liter fermentation broth is: 5.017×100=501.7 mg (calculating value×100=the content of total flavonoids per liter fermentation broth). The result is shown in FIG. 1.

Example 4

It is the same as the method described in Example 1, except that *Ganoderma lucidum* strain used in the example is Xinzhou *Ganoderma lucidum* (*Ganoderma lucidum*) strain which has a strain number of CGMCC No. 5.534, and the liquid fermentation culture in the step (2) is performed at 30° C. for 4 days, then adding an expansin solution to a concentration of 1.5 mg/mL to perform further culture for 6 days.

After calculated with the standard curve, the total flavonoids in the sample is 6.955 mg, i.e. the content of total flavonoids per liter fermentation broth is: 6.955×100=695.5 mg (calculating value×100=the content of total flavonoids per liter fermentation broth).

Comparative Example 1

It is the same as the method described in Example 1, except that in the step (2) no expansin solution is added, then performs further culture at 30° C. for 10 days.

After calculated with the standard curve, the total flavonoids in the sample is 1.107 mg, i.e. the content of total flavonoids per liter fermentation broth is: 1.107×100=110.7 mg (calculating value×100=the content of total flavonoids per liter fermentation broth). The result is shown in FIG. 1.

What is claimed is:

1. A method for improving the yield of flavonoids from *Ganoderma lucidum* mycelium, comprises the following steps of:
   (1) inoculating *Ganoderma lucidum* strains into a potato dextrose (PD) liquid fermentation medium comprising 200 g peeled potato, 20 g glucose and 1000 ml water; and performing activation culture to obtain a seed liquid;
   preparing an expansin solution by sterilizing a broad bean or cucumber seed with mercury chloride ($HgCl2$) for 4 to 6 minutes, washing with running water for 5 to 7 hours, culturing in the darkroom for 4 to 6 days at the temperature between 15 and 28° C.; precooling seedling hypocotyl apices for 0.5 hours at −20° C., adding a homogenate buffer solution that is pre-cooled to 4° C., filtering with a nylon net having an aperture of 70 μm after homogenate, washing the filter residue with a homogenate buffer solution, adding the filter residue in the homogenate buffer solution, settling for 1 to 3 hours to obtain a settled solution, adding an extracting solution in the settled solution for 44 to 50 hours at 4° C., adding 0.3 to 0.5 g/ml of ammonium sulfate (($NH_4)_2SO_4$) in the filtrate while stirring to prevent a partial supersaturation of the $(NH_4)_2SO_4$, settling for 25 to 30 hours centrifuging for 5 to 10 minutes at 4° C. dissolving the sediment with an acid buffer solution, dialyzing in a dialysis bag with a molecular weight of 3000 Da at 4° C., centrifuging the dialyzate at 20000 g for 10 minutes, and taking the supernatant to obtain the expansin solution;
   (2) inoculating the seed liquid obtained in step (1) into a liquid fermentation medium to perform liquid fermentation culture at the temperature between 25 and 30° C. for 3 to 5 days, then adding an expansin solution further culturing for additional 5 to 7 days, and separating to obtain *Ganoderma lucidum* mycelium, wherein the liquid fermentation medium has a pH between 5 and 7, and contains lactose, sucrose, soybean powder, peptone, yeast extract, $MgSO_4 \cdot 7H_2O$, $KH_2PO_4$; and
   (3) extracting flavonoids from the *Ganoderma lucidum* mycelium obtained in step (2), comprising the following steps:
   a) drying *Ganoderma lucidum* mycelium obtained in step (2) at 65° C. and grinding to power, b) adding ethanol solution up to 70-80% by volume and extracting by ultrasonic at 40 kHz and 200 W for 3 to 5 hours at the temperature between 60 and 70° C., then c) filtrating and separating the filtrate, and repeating 2 to 3 times of steps b) and c) for the precipitates; pooling the filtrates to yield the purified flavonoids.

2. The method according to claim 1, wherein the activation culture in step (1) is processed in the darkroom with a shaking speed of 100 to 180 r/min at the temperature between 25 to 30° C. for 3 to 5 days.

3. The method according to claim 1, wherein the concentration of expansin in step (2) is between 0.5 and 5 2.0 mg/mL.

4. The method according to claim 3, wherein the concentration of expansin in step (2) is between 0.75 and 1.75 mg/mL.

5. The method according to claim 4, wherein the concentration of expansin in step (2) is 1.5 mg/mL.

6. The method according to claim 1, wherein the homogenate buffer solution for the expansin solution has a pH between 6 and 8, and contains 15-35 mmol/L of 4-(2-hydroxyethyl)-1-iperazineethanesulfonic acid, 0.5-2.5 mmol/L of $Na2S20s$, 1-3 mmol/L of EDTA and 0.05-0.5% of Triton X-100; the extracting solution has a pH between 5-7, and contains 10-20 mmol/L of 4-(2-hydroxyethyl)-1-iperazineethanesulfonic acid, 0.5-2 mmol/L of ethylene diamine tetraacetic acid (EDTA), 0.5-2.5 mmol/L of Na2S20s and 0.1-1 of mmol/L NaCl; the acid buffer solution is prepared by dissolving of sodium acetate in water, the pH is adjusted between 3 to 5 with glacial acetic acid.

7. The method according to claim 1, wherein the separation in step (2) is carried out by centrifuging at 15000 rpm for 10 minutes at 4° C.

* * * * *